(12) United States Patent
Knuckey et al.

(10) Patent No.: US 8,492,048 B2
(45) Date of Patent: Jul. 23, 2013

(54) FUEL CELLS

(75) Inventors: Kathryn Knuckey, Ormskirk (GB); Andrew Creeth, Chester (GB)

(73) Assignee: Acal Energy Limited, Cheshire (GB)

( * ) Notice: Subject to any disclaimer, the term of this patent is extended or adjusted under 35 U.S.C. 154(b) by 876 days.

(21) Appl. No.: 12/374,352

(22) PCT Filed: Jul. 19, 2007

(86) PCT No.: PCT/GB2007/050420
§ 371 (c)(1),
(2), (4) Date: Dec. 30, 2009

(87) PCT Pub. No.: WO2008/009992
PCT Pub. Date: Jan. 24, 2008

(65) Prior Publication Data
US 2010/0112393 A1  May 6, 2010

(30) Foreign Application Priority Data

Jul. 19, 2006  (GB) .................................. 0614338.2

(51) Int. Cl.
| | |
|---|---|
| *H01M 8/10* | (2006.01) |
| *H01M 8/00* | (2006.01) |
| *H01M 8/24* | (2006.01) |
| *H01M 4/36* | (2006.01) |
| *H01M 8/08* | (2006.01) |
| *C07F 15/00* | (2006.01) |
| *C07F 17/02* | (2006.01) |

(52) U.S. Cl.
USPC ........... 429/483; 429/400; 429/465; 429/479; 429/480; 429/484; 429/491; 429/498; 556/138; 556/139; 556/143; 556/146

(58) Field of Classification Search
USPC ................. 429/465, 479, 480, 482, 484, 491, 429/400, 19, 46, 483, 498, 65; 556/138, 139, 556/143, 146
See application file for complete search history.

(56) References Cited

U.S. PATENT DOCUMENTS 3,152,013 A   10/1964 Juda
3,216,882 A *  11/1965 Feldt et al. .................... 428/131
(Continued)

FOREIGN PATENT DOCUMENTS

EP   0 043 647   1/1982
EP   0 228 168   11/1986
(Continued)

OTHER PUBLICATIONS

Corain et al. Abstract: Inorganica Chimica Acta vol. 157 No. 2 pp. 259-266.*
S.R. Alley and W. Henderson, "Synthesis and characterization of ferrocenyl-phosphonic and -arsonic acids," J. Organomet. Chem., 637-639, 2001, 216-229.
I. Bernal et al., "Iron(II) Complexes of Polydenate Aminopyridyl Ligands and an Exchangeable Sixth Ligand: Reactions with peroxides . . . " J. Chem. Soc., Dalton. Trans., 1995, 3667-3675.
(Continued)

*Primary Examiner* — Patrick Ryan
*Assistant Examiner* — Aaron Greso
(74) *Attorney, Agent, or Firm* — Knobbe Martens Olson & Bear LLP

(57) ABSTRACT

A redox fuel cell comprising an anode and a cathode separated by an ion selective polymer electrolyte membrane; means for supplying a fuel to the anode region of the cell; means for supplying an oxidant to the cathode region of the cell; means for providing an electrical circuit between the anode and the cathode; a catholyte solution comprising a modified ferrocene species being at least partially reduced at the cathode in operation of the cell, and at least partially re-generated by reaction with the oxidant after such reduction at the cathode.

20 Claims, 4 Drawing Sheets

U.S. PATENT DOCUMENTS

| | | | |
|---|---|---|---|
| 3,279,949 A | 10/1966 | Schaefer et al. | |
| 3,294,588 A | 12/1966 | Beltzer et al. | |
| 3,360,401 A | 12/1967 | Grasselli et al. | |
| 3,540,933 A | 11/1970 | Boeke | |
| 3,607,420 A | 9/1971 | Cutler | |
| 4,048,383 A | 9/1977 | Clifford | |
| 4,396,687 A | 8/1983 | Kummer et al. | |
| 4,952,289 A * | 8/1990 | Ciccone et al. | 205/633 |
| 5,250,158 A | 10/1993 | Kaneko et al. | |
| 5,298,343 A | 3/1994 | Savadogo et al. | |
| 5,660,940 A | 8/1997 | Larsson et al. | |
| 5,683,829 A | 11/1997 | Sarangapani | |
| 5,928,804 A * | 7/1999 | Leddy et al. | 429/10 |
| 5,958,616 A | 9/1999 | Salinas et al. | |
| 6,054,580 A | 4/2000 | Collins et al. | |
| 2001/0028977 A1 | 10/2001 | Kazacos et al. | |
| 2001/0033959 A1* | 10/2001 | Ovshinsky et al. | 429/40 |
| 2003/0059664 A1* | 3/2003 | Menjak et al. | 429/34 |
| 2003/0129469 A1* | 7/2003 | Sun et al. | 429/34 |
| 2003/0152823 A1 | 8/2003 | Heller | |
| 2004/0028203 A1 | 2/2004 | Wurster et al. | |
| 2004/0028989 A1* | 2/2004 | Sun et al. | 429/40 |
| 2004/0028992 A1 | 2/2004 | Jaouen | |
| 2004/0137297 A1 | 7/2004 | Matsuoka et al. | |
| 2005/0074653 A1 | 4/2005 | Broman | |
| 2005/0112055 A1 | 5/2005 | Shannon et al. | |
| 2005/0158618 A1 | 7/2005 | Liberatore et al. | |
| 2005/0164297 A1* | 7/2005 | Chen et al. | 435/7.1 |
| 2005/0244707 A1 | 11/2005 | Skyllas-Kazacos et al. | |
| 2006/0012637 A1 | 1/2006 | Furukawa et al. | |
| 2006/0024539 A1 | 2/2006 | Dumesic | |
| 2006/0088750 A1 | 4/2006 | Nobuta | |
| 2006/0134493 A1 | 6/2006 | Yoshida et al. | |
| 2006/0216565 A1 | 9/2006 | Cooray et al. | |
| 2007/0078052 A1 | 4/2007 | Grinberg et al. | |
| 2007/0122689 A1 | 5/2007 | Kubo et al. | |
| 2007/0131546 A1 | 6/2007 | Nomoto et al. | |
| 2008/0274385 A1 | 11/2008 | Creeth | |
| 2009/0308752 A1 | 12/2009 | Evans et al. | |
| 2009/0317668 A1 | 12/2009 | Creeth et al. | |
| 2009/0325002 A1 | 12/2009 | Creeth et al. | |
| 2010/0112388 A1 | 5/2010 | Creeth et al. | |
| 2010/0297522 A1 | 11/2010 | Creeth et al. | |
| 2011/0014532 A1 | 1/2011 | Knuckey et al. | |
| 2011/0027671 A1 | 2/2011 | Knuckey et al. | |
| 2011/0039170 A1 | 2/2011 | Creeth et al. | |
| 2011/0091746 A1 | 4/2011 | Knuckey et al. | |

FOREIGN PATENT DOCUMENTS

| | | |
|---|---|---|
| EP | 0 517 217 | 12/1992 |
| EP | 0 595 688 | 10/1993 |
| EP | 0 592 988 | 4/1994 |
| EP | 0 878 850 | 5/1998 |
| EP | 1 143 546 | 10/2001 |
| GB | 1 176 632 | 1/1970 |
| GB | 1 176 633 | 1/1970 |
| GB | 2 400 974 | 10/2004 |
| GB | 0505087.7 | 3/2005 |
| GB | 2 424 118 | 3/2006 |
| GB | 0605878.8 | 3/2006 |
| GB | 0608079.0 | 4/2006 |
| GB | 0614337.4 | 7/2006 |
| GB | 0614338.2 | 7/2006 |
| GB | 0718349.4 | 9/2007 |
| GB | 0718577.0 | 9/2007 |
| GB | 2 440 434 | 1/2008 |
| GB | 2 440 435 | 1/2008 |
| GB | 0801195.9 | 1/2008 |
| GB | 0801198.3 | 1/2008 |
| GB | 0801199.1 | 1/2008 |
| GB | 0907795.9 | 5/2009 |
| GB | 2 440 489 | 10/2009 |
| JP | 56 042970 | 4/1981 |
| JP | 57038906 | * 3/1982 |
| JP | 61 054163 | 3/1986 |
| JP | 62 015770 | 1/1987 |
| JP | 05-295578 | 11/1993 |
| JP | H05-295578 | * 11/1993 |
| JP | 11-288727 | 10/1999 |
| JP | 2004 319292 | 11/2004 |
| RU | 2004129396 | 3/2006 |
| WO | WO 91/13681 | 9/1991 |
| WO | WO 96/31912 | 10/1996 |
| WO | WO 00/12667 | 3/2000 |
| WO | WO 00/22688 | 4/2000 |
| WO | WO 00/29537 | 5/2000 |
| WO | WO 03/083967 | 10/2003 |
| WO | WO 2005/112055 | 11/2005 |
| WO | WO 2006/012637 | 2/2006 |
| WO | WO 2006/057387 | 6/2006 |
| WO | WO 2006/097438 | 9/2006 |
| WO | WO 2006/121191 | 11/2006 |
| WO | WO 2007/101284 | 9/2007 |
| WO | WO 01/73881 | 10/2007 |
| WO | WO 2007/110663 | 10/2007 |
| WO | WO 2007/122431 | 11/2007 |
| WO | WO 2008/009992 | 1/2008 |
| WO | WO 2008/009993 | 1/2008 |
| WO | WO 2009/037513 | 3/2009 |
| WO | WO 2009/040577 | 4/2009 |
| WO | WO 2009/093080 | 7/2009 |
| WO | WO 2009/093081 | 7/2009 |
| WO | WO 2009/093082 | 7/2009 |
| WO | WO 2010/128333 | 11/2010 |

OTHER PUBLICATIONS

J. Chang, et al., "Synthesis and Characterization of Bis(d-2-pyridylmethanamine)ruthenium(II)," Inorg Chem. 2004, 43, 1735-1742.

R. Dillon, S. Sdinivasan, A.S. Arico, V. Antonucci, "International Activities in DMFC R&D: status of technologies and potential applications," J. Power Sources, 127, 2004, 112-126.

W. R. Harris et al., "Chelating Tendencies of Pyridyl-Containing Polyamines and Oxygenation of the Cobaltous Complexes," Inorg. Chem., 1978, 17, 889-894.

A. Heinzel, V.M. Barragan, "A review of the state-of-the-art of the methanol crossover in direct methanol fuel cells," J. Power Sources, 84, 1999, 70-74.

M.P. Hogarth, T.R. Ralph, "Catalysis for Low Temperature Fuel Cells," Platinum Metal Reviews, 46, 2002, 146-164.

M. Klopstra, R. Hage, R.M. Kellogg and B.L. Feringa, "Non-heme iron catalysts for benzylic oxidation: a parallel ligand screening approach," Tet. Lett. 44, 2003, 4581-4584.

G.R. Knox and P.L. Pauson, "Ferrocene Derivatives, Part VII. Some Sulphur derivatives," J. Chem. Soc., 1958, 682.

Limoges, B.R. et al. "Electrocatalyst materials for fuel cells based on the polyoxometalates [PMo(12-n) Vn040]<(3+n)->(n=0-3)", Electrochimica Acta, Elsevier Scient Publishers, Barking, GB, vol. 50, No. 5, Jan. 15, 2005pp. 1169, 1170, 1176-1179.

M. Lubben et al., "Nonheme Iron Centers in Oxygen Activation: Characterization of an Iron(III) Hydroperoxide Intermediate," Angew. Chem. Int. Ed. Engl., 34, 1995, 1512-1514.

D. L. Reger et al. , "Synthesis and structural characterization of the bitopic ferrocene-based tris(pyrazolyl)methane ligand Fe[C5H4CH2OCH2C(pz)3]2 (pz=pyrazolyl ring)" J. Chem. Crystallography, 35, 2005, 217-225.

H. Sato et al., "Convenient Synthesis of N,N,N',N'Tetrakis(2-pyridylmethyl)-α,ω-alkanediamines Using a Phase-Transfer Catalyst," Synthesis, 1992, 539-540.

M. Tamura et al., "Superoxide Dismutase Activity of Iron(II) TPEN complex and Its Derivatives," Chem. Pharm. Bull., 48, 2000, 1514-1518.

M. Van den Heuval et al., "Synthesis of a Non-Heme Template for Attaching Four Peptides: An Approach to Artificial Iron(II)-Containing Peroxidases," J. Organ. Chem., 69, 2004. 250-262.

V. Neburchilov, J. Martin, H. Wang, J. Zhang, "A Review of Polymer Electrolyte Membranes for Direct Methanol Fuel Cells," Journal of Power Sources, 2007, vol. 169, pp. 221-238.

J.G. Roelfes, "Models for Non-Heme Iron Containing Oxidation Enzymes," Jun. 4, 1972, pp. 1-154.

* cited by examiner

FUEL CELLS

CROSS-REFERENCE TO RELATED APPLICATIONS

This Application is the US National Phase under 35 U.S.C. §371 of International Application No. PCT/GB2007/050420, filed Jul. 19, 2007, which was published in English as International Publication No. WO 2008/009992 on Jan. 24, 2008, and claims the benefit of GB 0614338.2, filed Jul. 19, 2006.

BACKGROUND

1. Field

The present invention relates to fuel cells, in particular to indirect or redox fuel cells which have applications as power sources for: portable products such as portable electronics products; for transport vehicles such as automobiles, both main and auxiliary; auxiliary power for caravans and other recreational vehicles, boats etc; stationary uses such as uninterruptible power for hospitals computers etc and combined heat and power for homes and businesses. The invention also relates to certain catholyte solutions for use in such fuel cells.

2. Description of the Related Art

Fuel cells have been known for portable applications such as automotive and portable electronics technology for very many years, although it is only in recent years that fuel cells have become of serious practical consideration. In its simplest form, a fuel cell is an electrochemical energy conversion device is that converts fuel and oxidant into reaction product(s), producing electricity and heat in the process. In one example of such a cell, hydrogen is used as fuel, and air or oxygen as oxidant and the product of the reaction is water. The gases are fed respectively into catalysing, diffusion-type electrodes separated by a solid or liquid electrolyte which carries electrically charged particles between the two electrodes. In an indirect or redox fuel cell, the oxidant (and/or fuel in some cases) is not reacted directly at the electrode but instead reacts with the reduced form (oxidized form for fuel) of a redox couple to oxidise it, and this oxidised species is fed to the cathode (anode for fuel).

There are several types of fuel cell characterised by their different electrolytes. The liquid electrolyte alkali electrolyte fuel cells have inherent disadvantages in that the electrolyte dissolves $CO_2$ and needs to be replaced periodically. Polymer electrolyte or PEM-type cells with proton-conducting solid cell membranes are acidic and avoid this problem. However, it has proved difficult in practice to attain power outputs from such systems approaching the theoretical maximum level, due to the relatively poor electrocatalysis of the oxygen reduction reaction.

In addition expensive noble metal electrocatalysts are often used. It would be preferable to use a less costly inert electrode, such as one formed of or coated with carbon, nickel or titanium. However, prior art cells in which inert electrodes have been utilised have produced unsatisfactory power output.

U.S. Pat. No. 3,152,013 discloses a gaseous fuel cell comprising a cation-selective permeable membrane, a gas permeable catalytic electrode and a second electrode, with the membrane being positioned between the electrodes and in electrical contact only with the gas permeable electrode. The electrodes are formed of platinum, iridium or other noble metal electrocatalysts. An aqueous catholyte is provided in contact with the second electrode and the membrane, the catholyte including an oxidant couple therein. Means are provided for supplying a fuel gas to the permeable electrode, and for supplying a gaseous oxidant to the catholyte for oxidising reduced oxidant material. The preferred catholyte and redox couple is $HBr/KBr/Br_2$. Nitrogen oxide is disclosed as a preferred catalyst for oxygen reduction, but with the consequence that pure oxygen was required as oxidant, the use of air as oxidant requiring the venting of noxious nitrogen oxide species.

An acknowledged problem concerning electrochemical fuel cells is that the theoretical potential of a given electrode reaction under defined conditions can be calculated but never completely attained. Imperfections in the system inevitably result in a loss of potential to some level below the theoretical potential attainable from any given reaction. Previous attempts to reduce such imperfections include the selection of mediators which undergo oxidation-reduction reactions in the catholyte solution. For example, U.S. Pat. No. 3,294,588 discloses the use of quinones and dyes in this capacity. However, despite the electrodes being coated with platinum, relatively low output was obtained during running of the cell. Another redox couple which has been tried is the vanadate/vanadyl couple, as disclosed in U.S. Pat. No. 3,279,949. In this case, the slow rate of reduction and oxidation of the vanadium couple reduces its performance. This problem is exacerbated by the insolubility of the vanadium couple. The same vanadium couple was used in U.S. Pat. No. 4,396,687.

According to U.S. Pat. No. 3,540,933, certain advantages could be realised in electrochemical fuel cells by using the same electrolyte solution for both catholyte and anolyte. This document discloses the use of a liquid electrolyte containing more than two redox couples therein, with equilibrium potentials not more than 0.8V apart from any other redox couple in the electrolyte.

The matching of the redox potentials of different redox couples in the electrolyte solution is also considered in U.S. Pat. No. 3,360,401, which concerns the use of an intermediate electron transfer species to increase the rate of flow of electrical energy from a fuel cell. The use of platinum coated electrodes is also disclosed.

U.S. Pat. No. 3,607,420 discloses an electrolyte in which the only soluble redox species present is the catalyst species. The electrolyte comprises a $Cu^{(I)}/Cu^{(II)}$ catalyst.

WO-A-2006/057387 discloses a bio fuel cell making use of a material which participates in the donation and receiving of electrons, the cell being said to exhibit an enhanced output power density. The material comprises an electron conductor of a specified external surface area, a redox polymer and a bio catalyst.

US-A-2003/0152823 discloses a fuel cell having an anode and a cathode with an anode enzyme disposed on the anode and a cathode enzyme disposed on the cathode.

US-A-2001/0028977 discloses a method for preparing a high energy density electrolyte solution for use in ore-vanadium redox cells.

Prior art fuel cells all suffer from one or more of the following disadvantages:

They are inefficient; they are expensive and/or expensive to assemble; they use expensive and/or environmentally unfriendly materials; they yield inadequate and/or insufficiently maintainable current densities and/or cell potentials; they are too large in their construction; they operate at too high a temperature; they produce unwanted by-products and/or pollutants and/or noxious materials; they have not found practical, commercial utility in portable applications such as automotive and portable electronics.

SUMMARY

It is an object of the present invention to overcome or ameliorate one or more of the aforesaid disadvantages. It is a further object of the present invention to provide an improved catholyte solution for use in redox fuel cells.

Accordingly, the present invention provides a redox fuel cell comprising an anode and a cathode separated by an ion selective polymer electrolyte membrane; means for supplying a fuel to the anode region of the cell; means for supplying an oxidant to the cathode region of the cell; means for providing an electrical circuit between the anode and the cathode; a catholyte solution comprising at least one non-volatile catholyte component flowing in fluid communication with the cathode, the catholyte solution comprising a modified ferrocene species which is at least partially reduced at the cathode in operation of the cell, and at least partially regenerated by, optionally indirect, reaction with the oxidant after such reduction at the cathode, and a redox catalyst catalysing the regeneration of the ferrocene mediator.

It has surprisingly been found that modified ferrocene species have the required properties to function effectively as redox couples in catholytes. Ferrocene itself is not able to do so as it is uncharged, insufficiently soluble and the $Fe^{(III)}$ form has a positive charge which makes it unsuitable for use in PEM cells including cation exchange membranes, such as Nafion™ membranes.

However chemical modifications of ferrocene improve its solubility and allow the charge of the species to be manipulated. Thus, if the modified ferrocene species is to be used as a catholyte in a PEM cell comprising a cation exchange membrane, it will preferably be non-ionic in its oxidized form or, more preferably, anionic.

Anionic charge can be introduced to ferrocene by modifying it with anionic is charge inducing groups such as carboxylate, phosphate or phosphonate groups. Stronger acid groups such as sulphonate and sulphate could also be introduced.

Alternatively, when the modified ferrocene species is to be used as a catholyte in a PEM cell comprising a anion exchange membrane, it will preferably be non-ionic in its reduced form, or more preferably, cationic.

Cationic charge can be introduced to ferrocene by modifying it with cationic charge inducing groups such as protonated amines or quaternary amine groups Thus, it can be seen that the charge of the modified ferrocene species of the present invention can be easily modified. This allows it to be tailored to the particular conditions of the cell with which it is to be used. For example, it can be tailored to the potential of the catholyte catalyst and the pH of the catholyte, and the charge of the exchangeable ions in the membrane.

Also provided in accordance with the invention is a catholyte solution for use in such a redox fuel cell.

The modified ferrocene species may be represented by the formula:

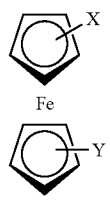

wherein:

X and Y are independently selected from hydrogen and from functional groups comprising halogen, hydroxy, amino, protonated amino, imino, nitro, cyano, acyl, acyloxy, sulphate, sulphonyl, sulphinyl, alkylamino, protonated alkylamino, quaternary alkylammonium, carboxy, carboxylic acid, ester, ether, amido, sulphonate, sulphonic acid, sulphonamide, phosphonic acid, phosphonate, phosphonic acid, phosphate, alkylsulphonyl, arylsulphonyl, alkoxycarbonyl, alkylsulphinyl, arylsulphinyl, alkylthio, arylthio, alkyl, alkoxy, oxyester, oxyamido, aryl, arylamino, aryloxy, heterocycloalkyl, heteroaryl, $(C_2\text{-}C_5)$alkenyl, $(C_2\text{-}C_5)$alkynyl, azido phenylsulphonyloxy or amino acid conjugates having the formula —CO—W—OH, where W is an amino acid, and from alkyl, alkenyl, aryl, cycloalkyl, alkaryl alkenaryl, aralkyl, aralkenyl groups substituted with one or more of the aforesaid functional groups.

The or each functional group may therefore be spaced from the ferrocene ring by any suitable number of spacer elements, for example alkyl, alkenyl, aryl, cycloalkyl, alkaryl alkenaryl, aralkyl or aralkenyl spacer elements, in which where appropriate any hydrocarbon chain may be straight or branched.

"Alkyl" is preferably $C_{1-6}$ alkyl, for example $C_{2-6}$ alkyl, $C_{1-5}$ alkyl, $C_{2-5}$ alkyl, $C_{1-4}$ alkyl, $C_{2-4}$ alkyl, $C_{1-3}$ alkyl, $C_{2-3}$ alkyl, $C_{1-2}$ alkyl. The same $C_{number}$ ranges apply to alkenyl groups and to the alkyl or alkenyl parts of any aralkyl, aralkenyl, alkaryl or alkenaryl groups.

Preferably, X and Y are independently selected from hydrogen and from functional groups comprising, halogen, hydroxy, amino, protonated amino, imino, acyl, sulphate, alkylamino, protonated alkylamino, quaternary alkylammonium, carboxy, carboxylic acid, ester, oxyester, alkoxy, sulphonyl, sulphinyl, alkylsulphonyl, sulphonic acid, sulphonamide, phosphonic acid, phosphonate, phosphate, amido, oxyamido or amino acid conjugates having the formula —CO—W—OH, where W is an amino acid, and from alkyl, alkenyl, aryl, cycloalkyl, alkaryl alkenaryl, aralkyl, aralkenyl groups substituted with one or more of the aforesaid functional groups.

More preferably, X and Y are independently selected from hydrogen and from functional groups comprising —F, —CHO, —COCH$_3$, —COCH$_2$CH$_3$, —COCH$_2$CH$_2$COOH, —COOH, —(COOH)$_2$, —NH$_2$, NH$_3^+$, —N(CH$_3$)$_2$, —NH(CH$_3$)$_2^+$, N(CH$_3$)$_3^+$, —N(CH$_2$CH$_3$)$_2$, —NH(CH$_2$CH$_3$)$^+$, —N(CH$_2$CH$_3$)$_3^+$, —CH$_2$N(CH$_3$)$_2$, —CH$_2$NH(CH$_3$)$_2^+$, —CH$_2$N(CH$_3$)$_3^+$, —OH, —CH$_2$OH, —CH(OH)CH$_3$, —OSO$_3^-$, —SO$_3^-$, —CH$_2$SO$_3^-$, —CH$_2$OSO$_3^-$, —PO(OH)$_2$, —OPO(OH)$_2$, —CO-Gly-OH, —CO-Glu-OH or —CO-Asp-OH, and from alkyl, alkenyl, aryl, cycloalkyl, alkaryl alkenaryl, aralkyl, aralkenyl groups substituted with one or more of the aforesaid functional groups.

There may be any number from 1 to 5 X substituents, in which case each X substituent may be the same or different. There may be any number from 1 to 5 Y substituents, in which case each Y substituent may be the same or different. All five X groups and all five Y groups cannot concomitantly be hydrogen.

The concentration of the modified ferrocene species in the catholyte solution is preferably at least about 0.0001M, more preferably at least about 0.005M, and most preferably at least about 0.001M.

The electrochemical properties of a number of catholytes comprising the modified ferrocene species of the present invention are shown in the following Table:

Measured Electrochemical Properties of Ferrocenes

| | Concentration | Solvent | pH | Oxidation/V | Reduction/V | Midpoint/V | Separation ΔEp/V |
|---|---|---|---|---|---|---|---|
| Fc-COOH | 0.005M | 0.1M NaOH | 13 | 0.32 | 0.24 | 0.28 | 0.08 |
| Fc-(COOH)$_2$ | 0.005M | 0.1M NaOH | 13 | 0.46 | 0.36 | 0.41 | 0.10 |
| Fc-CH$_2$NMe$_2$ | 0.005M | 0.01M H$_2$SO$_4$ | 1.85 | 0.41 | 0.33 | 0.37 | 0.08 |
| Fc-CH$_2$NMe$_2$ | 0.005M | H$_2$SO$_4$ | 0.4 | 0.36 | 0.3 | 0.33 | 0.06 |
| [1]Fc-CH$_2$NMe$_2$ | 0.005M | 0.001M H$_2$SO$_4$ | 10 | 0.23 | 0.15 | 0.19 | 0.08 |
| | | | | 0.39 | 0.33 | 0.36 | 0.06 |
| Fc-CH(OH)CH$_3$ | 0.001M | 10% MeOH 0.09 M KH$_2$PO$_4$ | 8 | 0.21 | 0.15 | 0.18 | 0.06 |
| *Fc-CH$_2$NMe$_3$+/− | 0.005M | Water | 6.7 | 0.51 | 0.31 | 0.41 | 0.20 |
| *Fc-CH$_2$NMe$_3$+/− | 0.005M | +H$_2$SO$_4$ | 2.46 | 0.50 | 0.33 | 0.42 | 0.17 |
| *Fc-CH$_2$NMe$_3$+/− | 0.005M | +H$_2$SO$_4$ | 0.97 | 0.45 | 0.37 | 0.41 | 0.08 |
| *Fc-CHO | 0.001M | 10% MeOH 0.09 M glycine | 2.5 | 0.534 | 0.45 | 0.492 | 0.08 |
| *Fc-CHO | 0.001M | 10% MeOH 0.09 M glycine + KOH to pH | 7.96 | 0.52 | 0.38 | 0.45 | 0.14 |
| Fc-CH$_2$—CN | Not soluble | | | | | | |
| Fc-(SO$_3$NH$_4$)$_2$ | 0.01M | 0.4M HCl | | 0.636 | 0.568 | 0.602 | 0.068 |
| Fc-(SO$_3$NH$_4$) | 0.01M | 0.4M HCl | | 0.406 | 0.343 | 0.375 | 0.063 |

*Not a simple CV-broad or two reduction peaks observed
[1]Two sets of oxidation/reduction peaks observed Preferred modified ferrocene species for use in the fuel cells of the invention include:

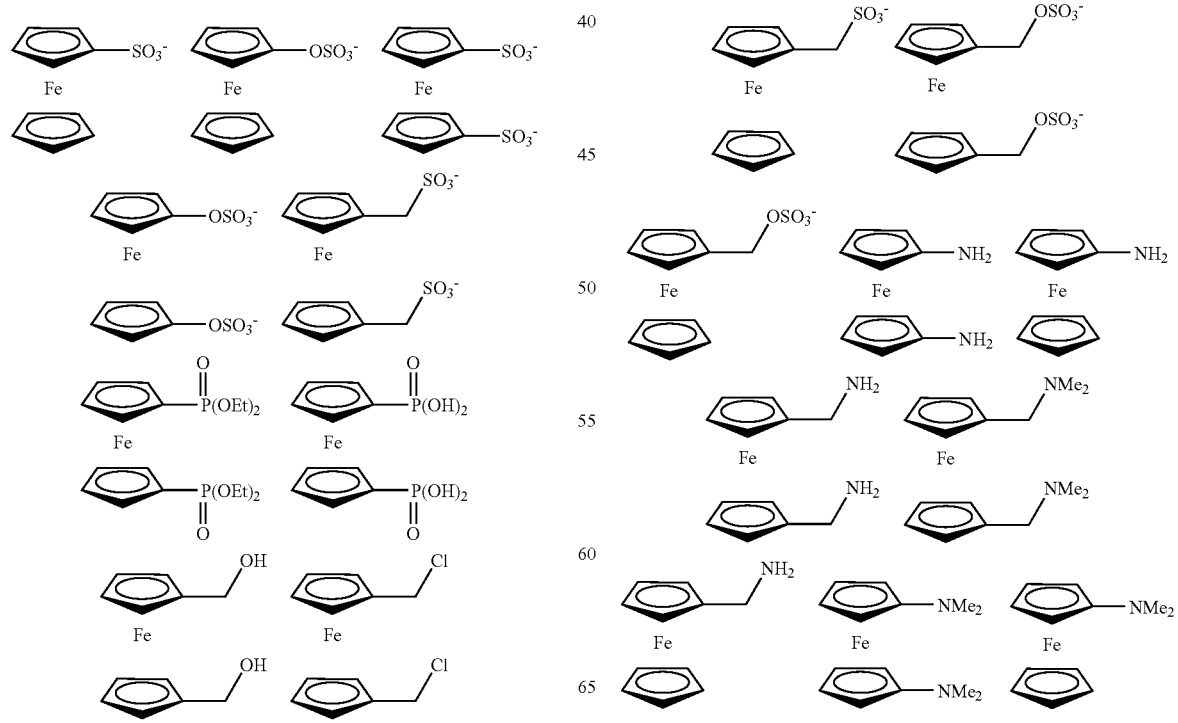

-continued

-continued

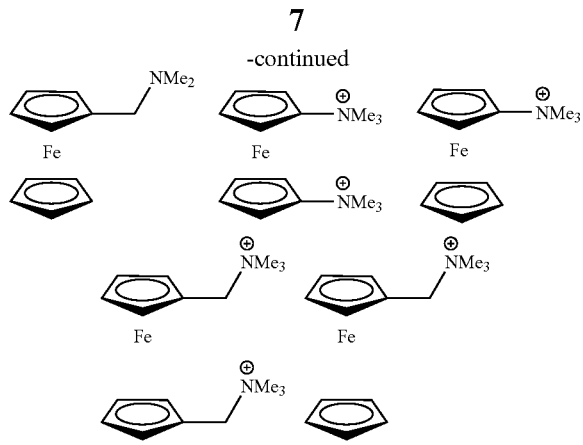

As part of the investigative work in connection with modified ferrocene species undertaken in relation to this invention, a novel material, namely 1,1'-bis(methylsulphonic acid)ferrocene, was synthesised.

According to the present invention, there is provided 1,1'-bis(methylsulphonic acid)ferrocene, and its use in the catholyte solution of a fuel cell in accordance with this invention.

Also provided in accordance with the present invention is a method of synthesising 1,1'-bis(methylsulphonic acid)ferrocene from 1,1'-Bis(chloromethyl)ferrocene in accordance with the following reaction scheme:

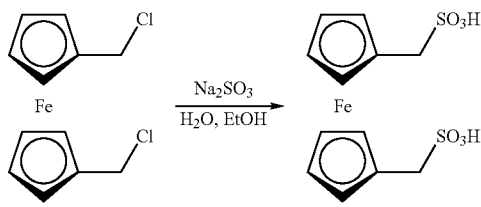

In one preferred embodiment of the invention, the ion selective PEM is a is a cation selective membrane which is selective in favour of protons versus other cations. In cases where the PEM is a cation selective membrane, the pH of the catholyte is preferably below 7, more preferably below 4, even more preferably below 2 and most preferably below 1.

The cation selective polymer electrolyte membrane may be formed from any suitable material, but preferably comprises a polymeric substrate having cation exchange capability. Suitable examples include fluororesin-type ion exchange resins and non-fluororesin-type ion exchange resins. Fluororesin-type ion exchange resins include perfluorocarboxylic acid resins, perfluorosulphonic acid resins, and the like. Perfluorocarboxylic acid resins are preferred, for example "Nafion" (Du Pont Inc.), "Flemion" (Asahi Gas Ltd), "Aciplex" (Asahi Kasei Inc), and the like. Non-fluororesin-type ion exchange resins include polyvinyl alcohols, polyalkylene oxides, styrene-divinylbenzene ion exchange resins, and the like, and metal salts thereof. Preferred non-fluororesin-type ion exchange resins include polyalkylene oxide-alkali metal salt complexes. These are obtainable by polymerizing an ethylene oxide oligomer in the presence of lithium chlorate or another alkali metal salt, for example. Other examples include phenolsulphonic acid, polystyrene sulphonic, polytrifluorostyrene sulphonic, sulphonated trifluorostyrene, sulphonated copolymers based on $\alpha,\beta,\beta$trifluorostyrene monomer, radiation-grafted membranes. Non-fluorinated membranes include sulphonated poly(phenylquinoxalines), poly(2,6-diphenyl-4-phenylene oxide), poly(arylether sulphone), poly(2,6-diphenylenol); acid-doped polybenzimidazole, sulphonated polyimides; styrene/ethylene-butadiene/styrene triblock copolymers; partially sulphonated polyarylene ether sulphone; partially sulphonated polyether ether ketone (PEEK); and polybenzyl suphonic acid siloxane (PBSS).

However, fuel cells of the present invention are not limited to use with only cationic selective polymer electrode membranes. Anionic selective polymer electrode membranes may also be used in the fuel cell of the present invention. Suitable examples of anionic membranes include quaternary amine derivatives of styrene cross-linked with divinyl benzene and polymerised in the presence of finely powdered polyvinyl chloride to provide strength.

In embodiments in which the polymer electrode membrane is anion specific, it is preferred that the catholyte solution have a pH of above 7. In a more preferred embodiment, the catholyte has a pH of above 8.

In some cases it may be desirable for the ion selective polymer electrolyte membrane to comprise a bi-membrane. The bimembrane if present will generally comprise a first cation selective membrane and a second anion selective membrane. In this case the bimembrane may comprise an adjacent pairing of oppositely charge selective membranes. For example the bimembrane may comprise at least two discrete membranes which may be placed side-by-side with an optional gap therebetween. Preferably the size of the gap, if any, is kept to a minimum in the redox cell of the invention. The use of a bi-membrane may be used in the redox fuel cell of the invention to maximise the potential of the cell, by maintaining the potential due to a pH drop between the anode and catholyte solution. Without being limited by theory, in order for this potential to be maintained in the membrane system, at some point in the system, protons must be the dominant charge transfer vehicle. A single cation-selective membrane may not achieve this to the same extent due to the free movement of other cations from the catholyte solution in the membrane.

In this case the cation selective membrane may be positioned on the cathode side of the bimembrane and the anion selective membrane may be positioned on the anode side of the bimembrane. In this case, the cation selective membrane is adapted to allow protons to pass through the membrane from the anode side to the cathode side thereof in operation of the cell. The anion selective membrane is adapted substantially to prevent cationic materials other than protons from passing therethrough from the cathode side to the anode side thereof. In this case protons may pass from anode to cathode.

In a second embodiment of the invention the cation selective membrane is positioned on the anode side of the bimembrane and the anion selective membrane is positioned on the cathode side of the bi-membrane. In this case, the cation selective membrane is adapted to allow protons to pass through the membrane from the anode side to the cathode side thereof in operation of the cell. In this case, anions can pass from the cathode side into the interstitial space of the bimembrane, and protons will pass from the anode side. It may be desirable in this case to provide means for flushing such protons and anionic materials from the interstitial space of the bimembrane. Such means may comprises one or more perforations in the cation selective membrane, allowing such flushing directly through the membrane. Alternatively means may be provided for channeling flushed materials around the cation selective membrane from the interstitial space to the cathode side of the said membrane.

A representative example of a useful bipolar membrane, the arrangement used with the anionic-selective membrane on the anode side is that sold under the trademark Neosepta® BP-1, available from Tokuyama Corporation.

According to another aspect of the present invention, there is provided a method of operating a proton exchange membrane fuel cell comprising the steps of:

a) forming $H^+$ ions at an anode situated adjacent to a proton exchange to membrane;
b) supplying the catholyte of the invention with its modified ferrocene species in an oxidised state to a cathode situated oppositely adjacent to the proton exchange membrane; and
c) allowing the modified ferrocene species to become reduced upon is contact with the cathode concomitantly with $H^+$ ions passing through the membrane to balance charge.

In another embodiment, the catholyte is supplied from a catholyte reservoir.

The method of the above fourth aspect may additionally comprise the step of:

d) passing the catholyte from the cathode to a reoxidation zone wherein the modified ferrocene species is reoxidised by the catalyst reacting with the oxidant.

In another embodiment, the method of the above aspect comprises the step of:

e) passing the catholyte from the reoxidation zone to the catholyte reservoir.

In this embodiment, the cell is cyclic and the modified ferrocene species in the cathode can be repeatedly oxidised and reduced without having to be replaced.

An electricity loading device configured to load an electric power may also be provided in association with the fuel cell of the invention.

The fuel cell of the invention may comprise a reformer configured to convert available fuel precursor such as LPG, LNG, gasoline or low molecular weight alcohols into a fuel gas (eg hydrogen) through a steam reforming reaction. The cell may then comprise a fuel gas supply device configured to supply the reformed fuel gas to the anode chamber.

Preferred fuels include hydrogen; metal hydrides, for example borohydride which may act as a fuel itself or as a provider of hydrogen, low molecular weight alcohols, aldehydes and carboxylic acids, sugars and biofuels as well as LPG, LNG or gasoline.

Preferred oxidants include air, oxygen and peroxides

The anode in the redox fuel cell of the invention may for example be a hydrogen gas anode or a direct methanol anode; other low molecular weight alcohols such as ethanol, propanol, dipropylene glycol; ethylene glycol; also aldehydes formed from these and acid species such as formic acid, ethanoic acid etc. In addition the anode may be formed from a bio-fuel cell type system where a bacterial species consumes a fuel and either produces a mediator which is oxidized at the electrode, or the bacteria themselves are adsorbed at the electrode and directly donate electrons to the anode.

The cathode in the redox fuel cell of the invention may comprise as cathodic material carbon, gold, platinum, nickel, metal oxide species. However, as a result of the advantageous catholyte of the present invention, the use of such cathodes is not necessary to achieve satisfactory power output. Thus, the preferred cathodic materials include carbon, nickel, titanium and other metals inert in the specific catholyte and metal oxide or sulphide. One preferable material for the cathodes is reticulated vitreous carbon or carbon fibre based electrodes such as carbon felt. Another is nickel foam or mesh, or titanium foam or mesh. The cathodic material may be constructed from a fine dispersion of particulate cathodic material, the particulate dispersion being held together by a suitable adhesive, or by a proton conducting polymeric material. The cathode is designed to create maximum flow of catholyte solution to the cathode surface. Thus it may consist of shaped flow regulators or a three dimensional electrode; the liquid flow may be managed in a flow-by arrangement where there is a liquid channel adjacent to the electrode, or in the case of the three dimensional electrode, where the liquid is forced to flow through the electrode. It is intended that the surface of the electrode is also the electrocatalyst, but it may be beneficial to adhere the electrocatalyst in the form of deposited particles on the surface of the electrode.

The modified ferrocene species flowing in solution in the cathode chamber in operation of the cell is used in the invention as a mediator which acts as an electron sink for electrons formed during the fuel cell reaction. Following this reduction of the mediator, it is reoxidised by the catalyst reacting with the oxidant.

The modified ferrocene species, and any catalyst redox couple, utilised in the fuel cell of the invention should be non-volatile, and be preferably soluble in aqueous solvent. Preferred catalyst couple species should react with the oxidant at a rate effective to generate a useful current in the electrical circuit of is the fuel cell, and react with the oxidant such that water is the ultimate end product of the reaction.

The fuel cell of the invention requires the presence of at least about 0.0001M of a modified ferrocene species in the catholyte solution. However, catalyst redox couples should be included in the catholyte solution in addition to the modified ferrocene species. There are many suitable examples of such catalyst redox couples, including ligated transition metal complexes and polyoxometallate species. Specific examples of polyoxometallate catalyst species which are useful in the fuel cell of the present invention are disclosed in the co-pending UK patent application, GB 0605878.8. Specific examples of suitable transition metals ions which can form such complexes include manganese (II-V), iron (I-IV), copper (I-III), cobalt (I-III), nickel (I-III), chromium (II-VII), titanium (II-IV), tungsten (IV-VI), vanadium (II-V) and molybdenum (II-VI). Ligands for ligated transition metal complexes can contain carbon, hydrogen, oxygen, nitrogen, sulphur, halides and/or phosphorus. Ligands may be chelating including EDTA, for example bound to iron or manganese metal centres, NTA, 2-hydroxyethylenediaminetriacetic acid, or non-chelating such as cyanide.

Alternative catalysts which may be useful in the present invention are complexes of multidentate N-donor ligands. Such ligands are described in our co-pending application GB 0614338.2 and may be coordinated with any suitable metal or metals, for example transition metals. Examples of such N-donor ligands can be selected from N4Py and derivatives thereof, pydien or derivatives thereof, and trilen and tpen and derivatives thereof. Iron complexes of these example N-donors are found to be effective catalysts for the oxidation of redox mediators in fuel cell systems. Other examples of such N-donor ligands may include one or more pyridine substituents.

BRIEF DESCRIPTION OF THE DRAWINGS

Various aspects of the present invention will now be more particularly described with reference to the following figures which illustrate embodiments of the present invention.

DETAILED DESCRIPTION

Figure 1:
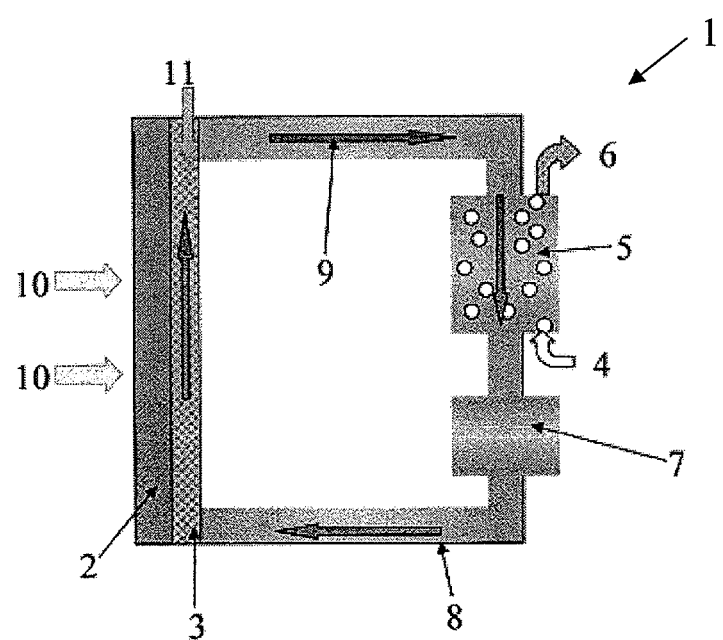
FIG. 1 illustrates a schematic view of the cathode compartment of a fuel cell in accordance with the present invention.

Referring to FIG. 1, there is shown the cathode side of fuel cell 1 in accordance with the invention comprising a polymer electrolyte membrane 2 separating an anode (not shown) from cathode 3. Cathode 3 comprises in this diagram reticulated carbon and is therefore porous. Polymer electrolyte membrane 2 comprises cation selective Nafion 112 membrane through which protons 10 generated by the (optionally catalytic) oxidation of fuel gas (in this case hydrogen) in the anode chamber pass in operation of the cell. Electrons 11 generated at the anode by the oxidation of fuel gas flow in an electrical circuit (not shown) and are returned to cathode 3. Fuel gas (in this case hydrogen) is supplied to the fuel gas passage of the anode chamber (not shown), while the oxidant (in this case air) is supplied to oxidant inlet 4 of cathode gas reaction chamber 5. Cathode gas reaction chamber 5 (the catalyst reoxidation zone) is provided with exhaust 6, through which the by-products of the fuel cell reaction (eg water and heat) can be discharged.

A catholyte solution comprising a catalyst and the oxidised form of the modified ferrocene species is supplied in operation of the cell from catholyte reservoir 7 into the cathode inlet channel 8. The catholyte passes into reticulated carbon cathode 3, which is situated adjacent membrane 2. As the catholyte passes through cathode 3, the modified ferrocene species and catalyst are reduced and are then returned to cathode gas reaction chamber 5 via cathode outlet channel 9.

Due to the advantageous composition of the catholyte of the present invention, reoxidation of the modified ferrocene species and the catalyst occurs very rapidly, which allows the fuel cell to produce a higher sustainable current than with catholytes of the prior art.

The following non-limiting examples describe the synthesis of a selection of substituted ferrocenes.

Example 1

Synthesis of Ferrocenesulphonic Acid Ammonium Salt

Prepared using the route described by Knox and Pauson in *J. Chem. Soc.,* 1958, 682.

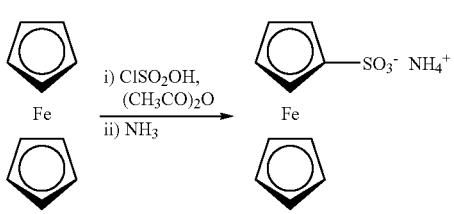

Example 2

Synthesis of 1,1'-bis(sulphonato)ferrocene diammonium salt

Prepared using the route described by Knox and Pauson in *J. Chem. Soc.,* 1958, 682.

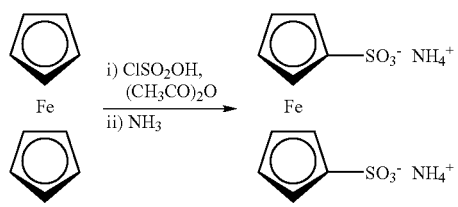

Example 3

Synthesis of 1,1'-bis(phosphonic acid)ferrocene (a) Synthesis of 1,1'-bis(diethylphosphonate)ferrocene Prepared using the route described by S. R. Alley and W. Henderson in *J. Organomet. Chem.,* 2001, 216.

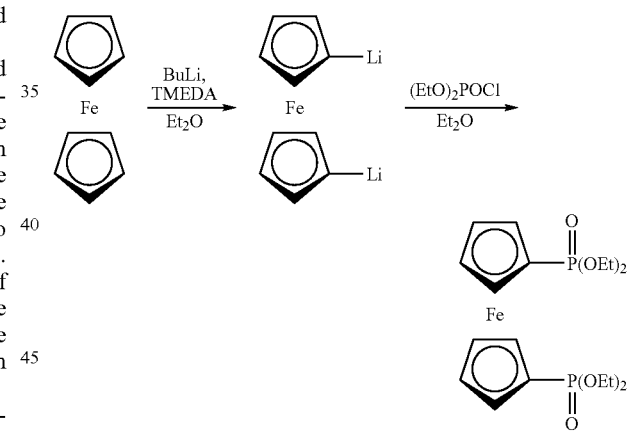

(b) Synthesis of 1,1'-bis(phosphonic acid)ferrocene

Prepared using the route described by S. R. Alley and W. Henderson in *J. Organomet. Chem.,* 2001, 216.

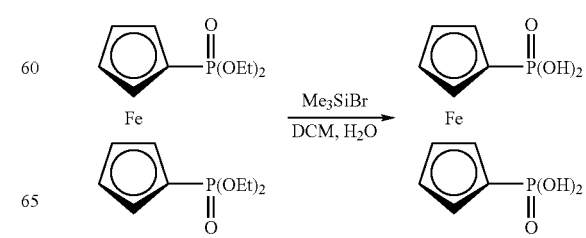

Example 4

Synthesis of 1,1'-bis(methylsulphonic acid)ferrocene (a) Synthesis of 1,1'-bis(chloromethyl)ferrocene Prepared using the procedure described by D. L. Reger et al in *J. Chem. Crystallography*, 2005, 35, 217.

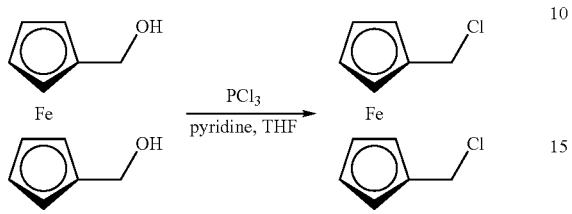

To a flask containing 1,1'-bis(hydroxymethyl)ferrocene (0.5 g, 2.0 mmol) under an atmosphere of nitrogen, was added THF (30 mL) and pyridine (0.33 mL, 4.1 mmol). PCl$_3$ (0.35 mL, 4.1 mmol) was added dropwise to this solution and a yellow precipitate immediately formed. The mixture was stirred at room temperature for 3 hours. The yellow solution was decanted from the solid using a syringe and the remaining solid was washed with THF (2×15 mL). The washings and original solution were combined and evaporated to dryness. The resulting residue was used immediately in subsequent reactions.

(b) Synthesis of 1,1'-bis(methylsulphonic acid)ferrocene

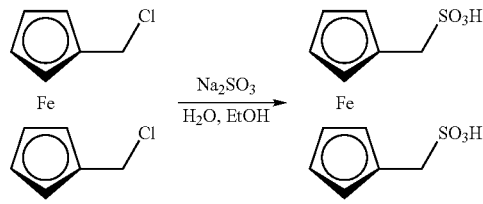

1,1'-Bis(chloromethyl)ferrocene (450 mg, 1.59 mmol) was dissolved in ethanol (10 mL) and treated with an aqueous solution of Na$_2$SO$_3$ (2.02 g, 16.0 mmol in 10 mL H$_2$O). The mixture was stirred at reflux for 3 days. The solvent was concentrated to ca. 5-10 mL before Dowex ion exchange resin 50WX8-200 (approx. 17 g) was added to the reaction mixture. The slurry was stirred at room temperature for 1½ hours. The Dowex was removed by filtration and washed with distilled water (3×25 mL). The aqueous washings were combined with the filtrate and evaporated in vacuo to a dark green solid. MS (ES$^-$): m/z=293 [M-SO$_3$H]; 186 [M]$^{2-}$.

A comparative test highlighting the improved performance of the catholyte of the present invention over prior art catholytes was performed as described in the following examples.

Example 5

A standard three electrode cell having (a) a 0.5 cm$^2$ glassy carbon electrode, (b) a reference calomel electrode (SCE) with a luggin capillary placed with the end about 2 mm away from the electrode, and (c) a platinum counter electrode was set up.

A cyclic voltammogram was ran at 50 mV/s at room temperature to compare the behaviour of two catholyte solutions. The first catholyte included 0.1M Fe(NO$_3$)$_3$ in 0.1M HNO$_3$. The second catholyte also included in addition a modified ferrocene species of the present invention, to (dimethylaminomethyl)ferrocene having the structure:

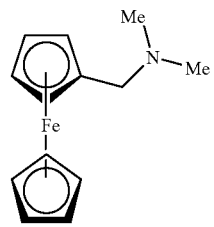

Figure 2:
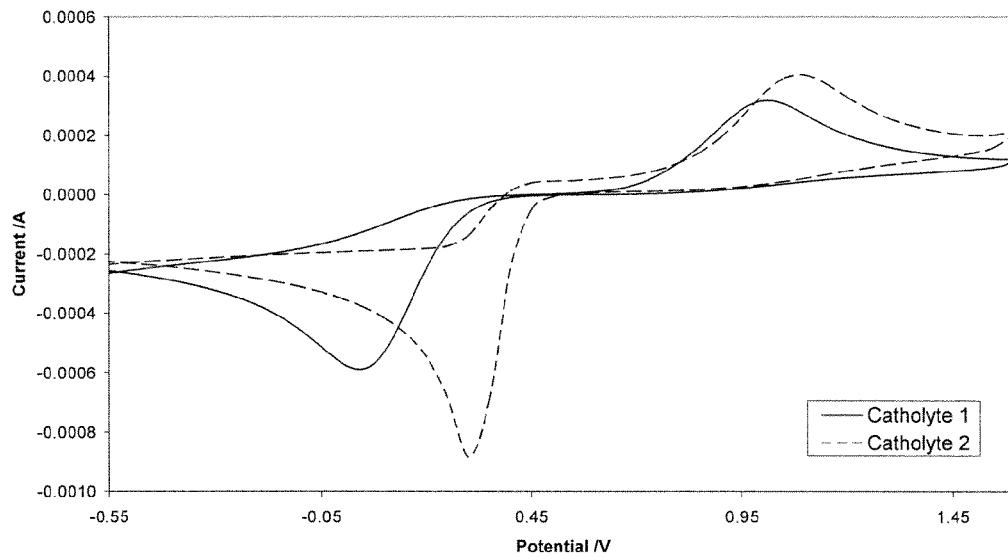
FIGS. 2 to 3 are graphs showing the results of certain comparative tests between catholytes of the present invention and of the prior art.

The Nernst potential of the first catholyte solution is 0.77V vs NHE, 0.53V vs SCE. The poor kinetics of the iron couple (Fe$^{(II)}$/Fe$^{(III)}$) are highlighted, as can be seen from FIG. 2, as significant reduction current does not occur until the potential reaches around 0.3 V vs SCE reaching a peak at about 0.05 V vs SCE. However, in the presence of the ferrocene, the current rises rapidly at around 0.4 V vs SCE to give a peak at between 0.3 and 0.35 V vs SCE.

Example 6

A similar experiment to that detailed in Example 5 was performed. However, the temperature at which the voltammogram was run was 75° C. Further, the composition of the catholytes differed in that the first catholyte included 0.1M FeCl$_3$ in 0.1M HCl and the second catholyte comprised the same solution together with 0.01M ferrocene monosulphonate having the structure:

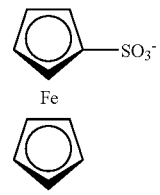

Figure 3:
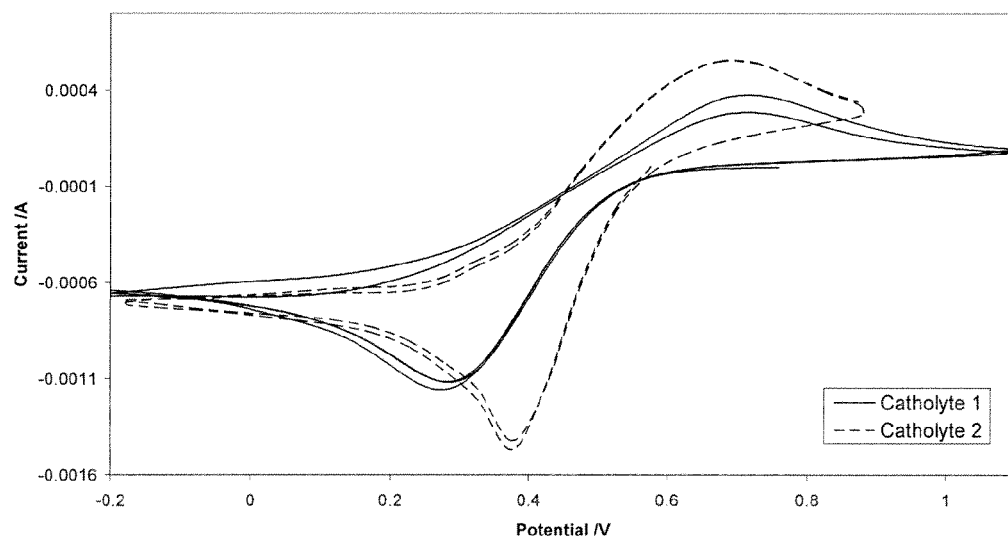

The results are shown in FIG. 3, from which it can be seen that the presence of the ferrocene in the second catholyte aids the reduction of iron (III) which increases the potential at which reduction occurs. The addition to the ferrocene of the sulphonate group renders it anionic, making it suitable for use in a fuel cell with a cation exchange membrane.

Example 7

In order to evaluate the use of transition metal complexes of N-donor ligands as oxygen reduction catalysts, the oxidation of a modified ferrocene species of the present invention, (dimethylaminomethyl)-ferrocene (Fc-CH$_2$NMe$_2$), by oxygen was studied at 55-60° C. in 0.1M glycine buffer solution at pH 2.5. The reaction can be illustrated as follows:

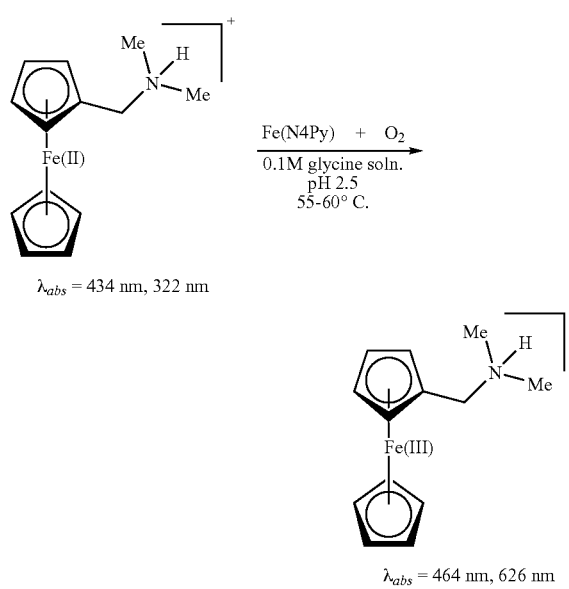

$\lambda_{abs}$ = 434 nm, 322 nm $\lambda_{abs}$ = 464 nm, 626 nm

Experiments were carried out using varying concentrations (0.3 mM and 1.0 mM) of Fe(N4Py) catalyst, generated in situ by combining 0.1M glycine solutions of FeSO$_4$.7H$_2$O and [N4Py-H]$^+$[PF$_6$]$^-$ at pH 2.5.

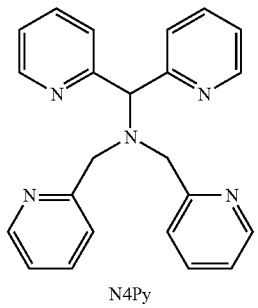 [SMILES: c1ccc(CN(Cc2ccccn2)C(c2ccccn2)c2ccccn2)nc1]

N4Py

An uncatalysed oxidation experiment was also performed under the same conditions as a control experiment. Oxygen was bubbled through 100 mL of solution containing 15 mM (dimethylaminomethyl)-ferrocene and samples were removed at regular time intervals (measured in minutes) in order to monitor the production of the oxidised ferrocene species via the UV-Vis absorption is peak at 626 nm. This data is summarised in the table below, which shows that oxidation of the Fc-CH$_2$NMe$_2$ mediator is catalysed by the Fe(N4Py) catalyst.

| Experiment | Uncatalysed | 0.3 mM Fe(N4Py) | 1.0 mM Fe(N4Py) |
|---|---|---|---|
| Initial rate of mediator oxidation/×10$^{-6}$ Ms$^{-1}$ | 0.13 | 0.34 | 1.4 |

Example 8

A catalytic experiment was conducted to monitor the ability of a transition metal catalyst to bring about the oxidation of a modified ferrocene species of the present invention, ferrocenesulphonic acid ammonium salt, by oxygen. The experiment was conducted at ~65° C. in 0.1M glycine buffer solution at pH 2.5.

A solution containing 1.0 mM of Fe(trilen) catalyst was generated in situ by combining 0.1M glycine solutions of FeSO$_4$.7H$_2$O and trilen at pH 2.5.

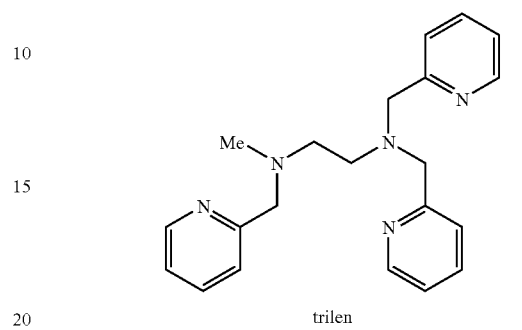

trilen

An uncatalysed oxidation experiment was also performed under the same conditions as a control experiment. Oxygen was bubbled through 100 mL of solution containing 15 mM ferrocenesulphonic acid ammonium salt and samples were removed at regular time intervals (measured in minutes) in order to monitor the production of the oxidised ferrocene species via the UV-V is absorption peak at 627 nm. This data is summarised in the table below and shows that Fe(trilen) acts as an efficient catalyst for the oxidation of ferrocenesulphonic acid ammonium salt.

| Experiment | Uncatalysed | 1.0 mM Fe(trilen) |
|---|---|---|
| Initial rate of mediator oxidation/×10$^{-6}$ Ms$^{-1}$ | 0.044 | 14.5 |

Example 9

A catalytic experiment was conducted to monitor the ability of a transition metal catalyst to bring about the oxidation of a modified ferrocene species of the present invention, 1,1'-bis(methylsulphonic acid)ferrocene, by oxygen. The experiment was conducted at ~65° C. in an aqueous solution containing 0.05 M Na$_2$SO$_4$ and 0.05 M NaHSO$_4$ adjusted to pH 2.5.

A solution containing 1.0 mM of Fe(trilen) catalyst was generated in situ by combining solutions of FeSO$_4$.7H$_2$O and trilen.

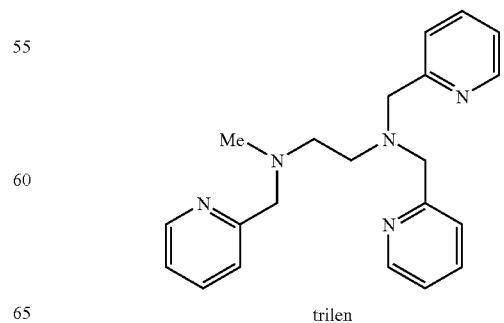

trilen

An uncatalysed oxidation experiment was also performed under the same conditions as a control experiment. Oxygen was bubbled through 25 mL of solution containing 10 mM 1,1'-bis(methylsulphonic acid)-ferrocene and samples were removed at regular time intervals (measured in minutes) in order to monitor the production of the oxidised ferrocene species via the UV-V is absorption peak at 650 nm. This data is summarised in the table below and shows that Fe(trilen) acts as an efficient catalyst for the oxidation of 1,1'-bis(methylsulphonic acid)-ferrocene.

| Experiment | Uncatalysed | 1.0 mM Fe(trilen) |
|---|---|---|
| Change in absorption at 650 nm after 3 minutes | 0.003 | 0.270 |

Example 10

A catalytic experiment was conducted to monitor the ability of the iron complex of N-donor ligand N-methyl-N,N',N',-tris(2-(4-sulphonato)-pyridylmethyl)ethane-1,2-diamine trisodium salt (Fe(trilen-$(SO_3Na)_3$)) to bring about the oxidation of 1,1'-bis(methylsulphonato)ferrocene disodium salt, by oxygen.

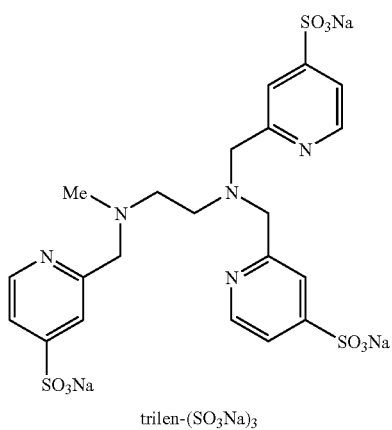

trilen-$(SO_3Na)_3$

Figure 4:
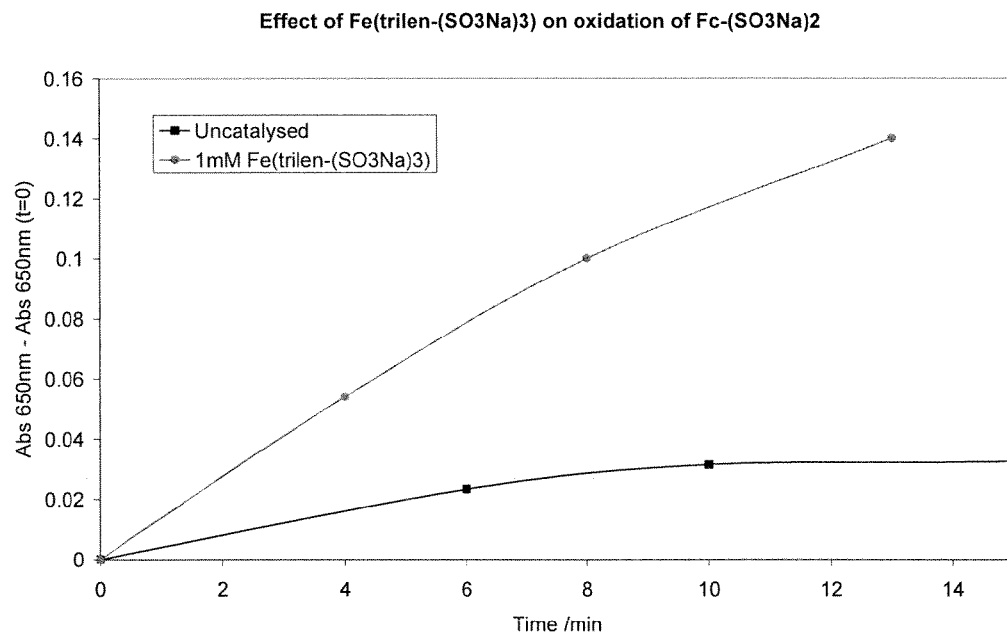
FIG. 4 shows that Fe(trilen-(SO₃Na)₃) acts as a catalyst for the oxidation of 1,1'-bis(methylsulphonato)ferrocene disodium salt.

A catalytic experiment was conducted using a solution containing 1.0 mM of Fe(trilen-$(SO_3Na)_3$), 10 mM of mediator species 1,1'-bis(methylsulphonato)-ferrocene disodium salt [Fc-$(CH_2SO_3Na)_2$] and 0.1 M glycine buffer at pH 2.5. The solution was heated to 65° C. and bubbled with oxygen. The reaction was monitored by UV-Vis absorption spectroscopy to measure the increase in absorption at 650 nm. An uncatalysed oxidation experiment was also performed under the same conditions as a control experiment. This data is summarised in FIG. 4 and shows that Fe(trilen-$(SO_3Na)_3$) acts as a catalyst for the oxidation of 1,1'-bis(methylsulphonato)ferrocene disodium salt.

Example 11

A catholyte solution of the present invention was prepared and its performance assessed using a redox cathode and a hydrogen anode. A commercial anode was used with a platinised gas diffusion layer from E-TEK (De Nora Deutschland), ½ MEA from Ion Power Inc using a 0.05 mm is Nafion™ (DuPont) membrane. A reticulated vitreous carbon (RVC) electrode was used for the cathode. The catholyte solution was pumped through this electrode before passing to a reservoir from where it was recirculated. The total liquid volume was 25 cm³.

Figure 5:
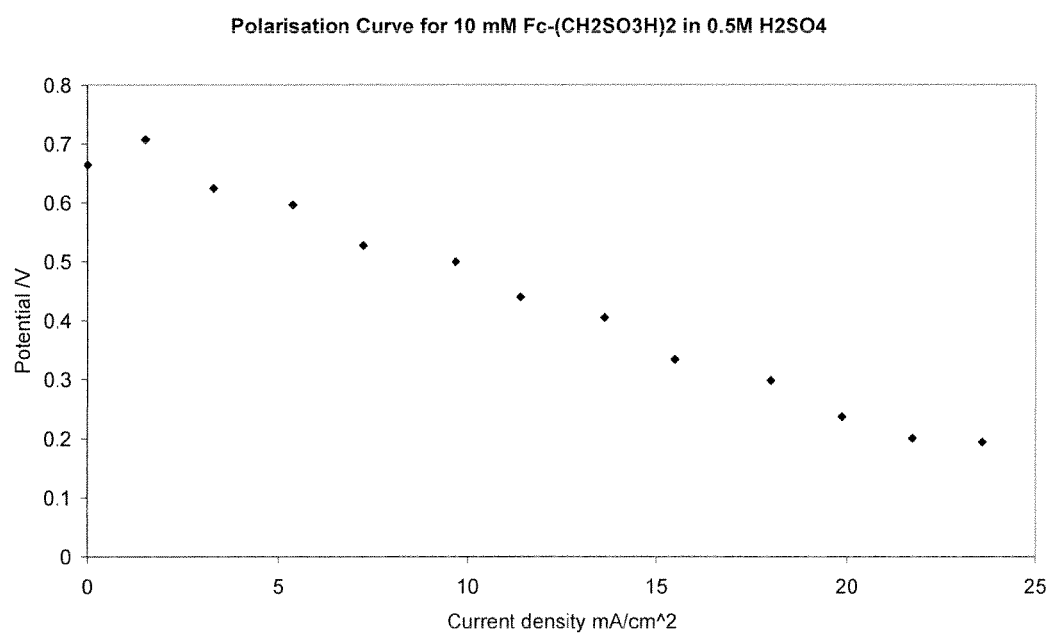
FIG. 5 shows a polarisation curve of a catholyte solution in accordance with the invention.

The catholyte solution tested contained 1,1'-bis(methylsulphonic acid)-ferrocene (101 mg) in 0.5 M $H_2SO_4$ (25 mL). The partially oxidised solution (absorbance of 0.53 at 652 nm) was flowed through the cell whilst a polarisation curve was recorded. This can be seen in FIG. 5.

Example 12

A catholyte solution of the present invention was prepared and its performance assessed using a redox cathode and a hydrogen anode. A commercial anode was used with a platinised gas diffusion layer from E-TEK (De Nora Deutschland), ½ MEA from Ion Power Inc using a 0.125 mm is Nafion™ (DuPont) membrane. A reticulated vitreous carbon (RVC) electrode was used for the cathode. The catholyte solution was pumped through this electrode before passing to a reservoir from where it was recirculated. The total liquid volume was 25 cm³.

Figure 6:
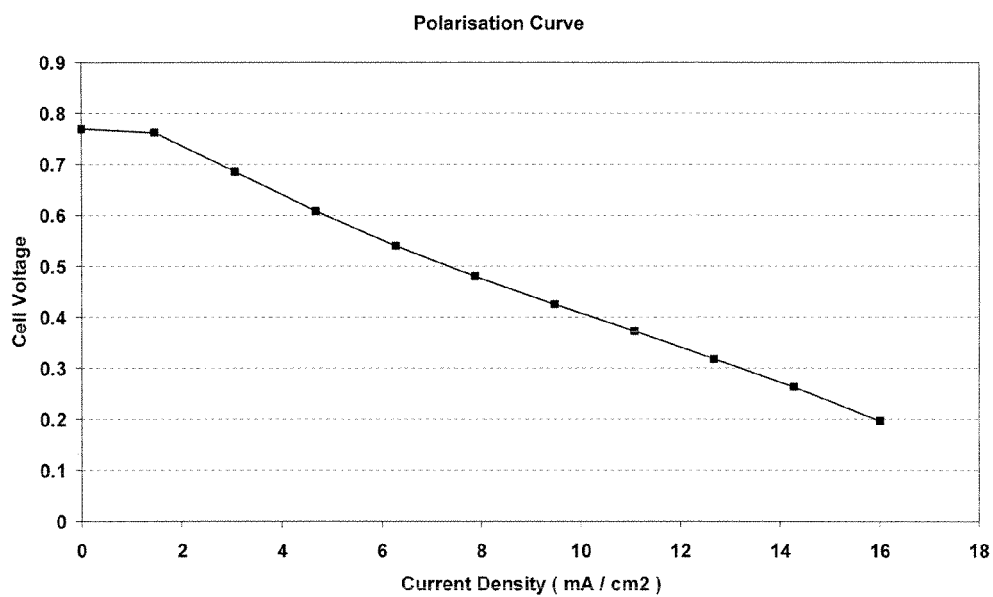
FIG. 6 shows a further polarisation curve of a catholyte solution in accordance with the invention.

The catholyte solution tested contained 10 mM 1,1'-bis(methylsulphonato)-ferrocene disodium salt and 1.0 mM Fe(trilen-$(SO_3Na)_3$) in a buffer solution containing 0.05 M $Na_2SO_4$ and 0.05M $NaHSO_4$ at pH 2. The catholyte was partially oxidised by bubbling oxygen through the solution at 65° C. for 30 minutes whereupon the absorbance at 650 nm was measured as 0.24. This resulting solution was flowed through the fuel cell whilst a polarisation curve was recorded. This can be seen in FIG. 6.

Figure 7:
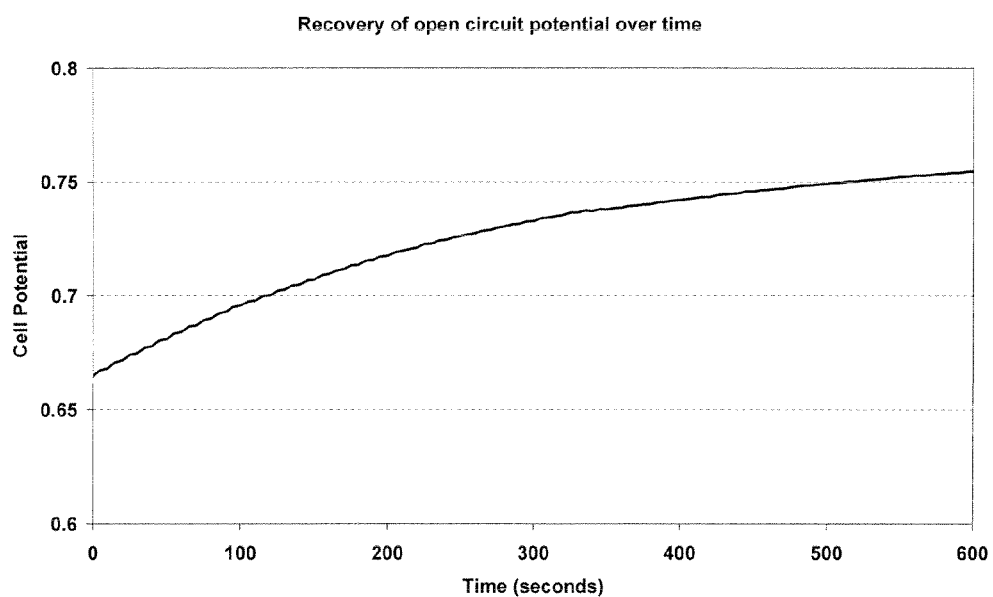
FIG. 7 shows the ability of a catholyte in accordance with the invention to regenerate, assessed by monitoring the recovery of the open circuit potential whilst bubbling oxygen through the catholyte.

The solution was partially reduced in the fuel cell by drawing a current over a period of several minutes. The ability of the catholyte to regenerate was then assessed by monitoring the recovery of the open circuit potential whilst bubbling oxygen through the catholyte. This data can be seen in FIG. 7.

The invention claimed is:
1. A redox fuel cell comprising:
   an anode region comprising an anode and a cathode region comprising a cathode, said regions being separated by an ion selective polymer electrolyte membrane;
   a fuel passage through which fuel is supplied to the anode region of the cell;
   an oxidant inlet that supplies an oxidant to the cathode region of the cell;
   an electrical circuit between the anode and the cathode; and
   a catholyte solution flowing in fluid communication with the cathode, the catholyte solution comprising a modified ferrocene species, the modified ferrocene species being at least partially reduced at the cathode in operation of the cell, and at least partially re-generated by reaction with the oxidant isolated from the anode region after said reduction at the cathode.
2. A redox fuel cell according to claim 1 wherein the modified ferrocene species is represented by the formula:

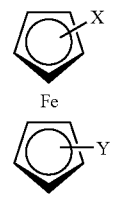

wherein:
X and Y are independently selected from the group consisting of hydrogen and functional groups comprising halogen, hydroxy, amino, protonated amino, imino, nitro, cyano, acyl, acyloxy, sulphate, sulphonyl, sulphinyl, alkylamino, protonated alkylamino, quaternary alkylammonium, carboxy, carboxylic acid, ester, ether, amido, sulphonate, sulphonic acid, sulphonamide, phosphonic acid, phosphonate, phosphonic acid, phosphate, alkylsulphonyl, arylsulphonyl, alkoxycarbonyl, alkylsulphinyl, arylsulphinyl, alkylthio, arylthio, alkyl, alkoxy, oxyester, oxyamido, aryl, arylamino, aryloxy, heterocycloalkyl, heteroaryl, ($C_2$-$C_5$)alkenyl, ($C_2$-$C_5$) alkynyl, azido phenylsulphonyloxy or amino acid conjugates having the formula —CO—W—OH, where W is an amino acid, and from alkyl, alkenyl, aryl, cycloalkyl, alkaryl alkenaryl, aralkyl, aralkenyl groups substituted with one or more of the aforesaid functional groups.

3. A redox fuel cell according to claim 2, wherein X and Y are independently selected from the group consisting of hydrogen and functional groups comprising, halogen, hydroxy, amino, protonated amino, imino, acyl, sulphate, alkylamino, protonated alkylamino, quaternary alkylammonium, carboxy, carboxylic acid, ester, oxyester, alkoxy, sulphonyl, sulphinyl, alkylsulphonyl, sulphonic acid, sulphonamide, phosphonic acid, phosphonate, phosphate, amido, oxyamido, or amino acid conjugates having the formula —CO—W—OH, where W is an amino acid, and from alkyl, alkenyl, aryl, cycloalkyl, alkaryl alkenaryl, aralkyl, aralkenyl groups substituted with one or more of the aforesaid functional groups.

4. A redox fuel cell according to claim 2 wherein X and Y are independently selected from the group consisting of hydrogen and from functional groups comprising —F, —CHO, —COCH$_3$, —COCH$_2$CH$_3$, —COCH$_2$CH$_2$COOH, —COOH, —(COOH)$_2$, —NH$_2$, —NH$_3^+$, —N(CH$_3$)$_2$, —NH(CH$_3$)$_2^+$, —N(CH$_3$)$_3^+$, —N(CH$_2$CH$_3$)$_2$, —NH(CH$_2$CH$_3$)$^+$, —N(CH$_2$CH$_3$)$_3^+$, —CH$_2$N(CH$_3$)$_2$, —CH$_2$NH(CH$_3$)$_2^+$, —CH$_2$N(CH$_3$)$_3^+$, —OH, —CH$_2$OH, —CH(OH)CH$_3$, —OSO$_3^-$, —SO$_3^-$, —CH$_2$SO$_3^-$, —CH$_2$OSO$_3^-$, —PO(OH)$_2$, —OPO(OH)$_2$, —CO-Gly-OH, —CO-Glu-OH or —CO-Asp-OH, and from alkyl, alkenyl, aryl, cycloalkyl, alkaryl alkenaryl, aralkyl, aralkenyl groups substituted with one or more of the aforesaid functional groups.

5. A redox fuel cell according to claim 1 wherein the ion selective polymer electrode membrane is cation and/or proton selective.

6. A redox fuel cell according to claim 5 wherein the catholyte solution is acidic.

7. A redox fuel cell according to claim 5 wherein the ferrocene is non-ionic or anionic in its oxidized form.

8. A redox fuel cell according to claim 1 wherein the ion selective polymer electrode membrane is anion selective.

9. A redox fuel cell according to claim 8 wherein the catholyte solution is alkali.

10. A redox fuel cell according to claim 8 wherein the ferrocene is non-ionic or cationic in its reduced form.

11. A redox fuel cell according to claim 1 wherein the ion selective polymer electrode membrane is a bi-membrane.

12. A redox fuel cell according to claim 1 wherein the modified ferrocene species is present in the catholyte solution at a concentration of at least 0.0001 M.

13. A redox fuel cell according to claim 1 wherein the modified ferrocene species is present in the catholyte solution at a concentration of at least 0.005M.

14. A redox fuel cell according to claim 1 wherein the modified ferrocene species is present in the catholyte solution at a concentration of at least 0.001 M.

15. A redox fuel cell according to claim 1 wherein the catholyte solution additionally comprises a catalyst redox species.

16. A redox fuel cell according to claim 15 wherein the catalyst redox species is selected from the group consisting of ligated transition metal complexes, polyoxometallate species, and combinations thereof.

17. A redox fuel cell according to claim 16 wherein the transition metal(s) in the transition metal complexes are selected from the group consisting of manganese (II-V), iron (I-IV), copper (I-III), cobalt (I-III), nickel (I-III), chromium (II-VII), titanium (II-IV), tungsten (IV-VI), vanadium (II-V) and molybdenum (II-VI).

18. A redox fuel cell according to claim 15 wherein the catalyst redox species comprises a multidentate N-donor ligand.

19. A redox fuel cell according to claim 18 wherein the N-donor ligand comprises one or more pyridine substituents.

20. A redox fuel cell according to claim 18 wherein the catalyst redox species is selected from the group consisting of iron complexes of N4Py (N,N-bis(pyridine-2-yl-methyl)-bis (pyridine-2-yl)methylamine) and derivatives thereof, pydien (1,9-bis(2-pyridyl)-2,5,8-triazanonane) and derivatives thereof, trilen (N-methyl-N,N',N'-tris(2-pyridylmethyl) ethane-1,2-diamine) and derivatives thereof, and tpen (N,N', N',N'-Tetrakis(2-pyridylmethyl)ethane-1,2-diamine) and derivatives thereof.

\* \* \* \* \*